United States Patent
Brown (10) Patent No.: US 10,398,508 B2
(45) Date of Patent: *Sep. 3, 2019

(54) PROTECTIVE SHEATH AND METHOD OF USING SAME FOR LASER SURGERY

(71) Applicant: Joe Denton Brown, Panama City, FL (US)

(72) Inventor: Joe Denton Brown, Panama City, FL (US)

( * ) Notice: Subject to any disclaimer, the term of this patent is extended or adjusted under 35 U.S.C. 154(b) by 463 days.

This patent is subject to a terminal disclaimer.

(21) Appl. No.: 13/761,960

(22) Filed: Feb. 7, 2013

(65) Prior Publication Data

US 2013/0218147 A1   Aug. 22, 2013

Related U.S. Application Data (60) Provisional application No. 61/721,184, filed on Nov. 1, 2012, provisional application No. 61/674,058, filed on Jul. 20, 2012, provisional application No. 61/596,000, filed on Feb. 7, 2012.

(51) Int. Cl.
*A61B 18/20* (2006.01)
*A61B 18/22* (2006.01)
*A61B 18/00* (2006.01)

(52) U.S. Cl.
CPC .... *A61B 18/22* (2013.01); *A61B 2018/00107* (2013.01)

(58) Field of Classification Search
CPC .... D02G 3/00; G02B 6/06; G01S 5/02; H05B 6/50; A61B 18/18; A61N 5/06
USPC ............ 606/1–19; 607/88–94; 428/372, 373; 385/117; 342/417; 219/713
See application file for complete search history.

(56) References Cited

U.S. PATENT DOCUMENTS

| | | | | |
|---|---|---|---|---|
| 3,658,634 A | * | 4/1972 | Yanagi et al. | 428/373 |
| 4,223,226 A | * | 9/1980 | Quick et al. | 250/458.1 |
| 4,441,788 A | * | 4/1984 | Guerder | C03B 37/014 385/124 |
| 4,448,547 A | * | 5/1984 | Wickersheim | G01J 5/48 250/337 |

(Continued)

FOREIGN PATENT DOCUMENTS

| | | |
|---|---|---|
| WO | WO2010/053575 A2 | 5/2010 |
| WO | WO 2010053575 A2 * | 5/2010 |

OTHER PUBLICATIONS

R. Passy, N. Gisin, and J. P. von der Weid, High-Sensitivity-Coherent Optical FrequencyDomain Reflectometry, IEEE Photonics Technology Letters, vol. 7, No. 6, Jun. 1995.*

(Continued)

*Primary Examiner* — Lynsey C Eiseman
(74) *Attorney, Agent, or Firm* — Bacon & Thomas, PLLC (57) ABSTRACT

A protective sheath is provided to prevent mechanical damage to the working channel of the endoscope during insertion of the fiber, insulate the fiber from surrounding cooling fluids, and/or serve as an indicator of overheating that enables early detection of excess heating or burning of tissues or equipment at the treatment site. The protective sheath may include trim markings to facilitate cutting to a desired length, such as the length of the fiber in the scope, may also be arranged to glow when the fiber is pulled too far into the sheath, may be tightly fitted over the fiber to provide a plunger effect, and may include perforations to facilitate sterilization.

5 Claims, 6 Drawing Sheets

(56) References Cited

U.S. PATENT DOCUMENTS

| | | | | |
|---|---|---|---|---|
| 4,518,839 A | * | 5/1985 | Taguchi et al. | 219/713 |
| 4,626,068 A | * | 12/1986 | Caldwell | G02B 6/443 250/458.1 |
| 4,679,934 A | * | 7/1987 | Ganguly et al. | 356/43 |
| 4,776,827 A | * | 10/1988 | Greaves | G01K 11/3213 250/461.1 |
| 4,890,898 A | * | 1/1990 | Bentley | G01K 17/003 374/E17.002 |
| 4,892,380 A | * | 1/1990 | Mori | G02B 6/3825 385/58 |
| 5,057,099 A | * | 10/1991 | Rink | 606/12 |
| 5,163,935 A | | 11/1992 | Black et al. | |
| 5,359,685 A | | 10/1994 | Waynant et al. | |
| 5,458,596 A | * | 10/1995 | Lax | A61B 18/148 606/31 |
| 5,672,153 A | * | 9/1997 | Lax | A61B 10/0233 604/22 |
| 5,843,000 A | * | 12/1998 | Nishioka | A61B 10/06 600/104 |
| 5,865,788 A | * | 2/1999 | Edwards | A61B 18/00 604/22 |
| 5,902,251 A | * | 5/1999 | vanHooydonk | A61B 18/18 600/549 |
| 5,935,075 A | * | 8/1999 | Casscells | A61B 5/0086 600/474 |
| 6,011,889 A | * | 1/2000 | Daniel et al. | 385/117 |
| 6,437,741 B1 | * | 8/2002 | Fox | 342/417 |
| 6,458,120 B1 | | 10/2002 | Shen et al. | |
| 6,911,258 B1 | * | 6/2005 | Prigent et al. | 428/372 |
| 8,277,119 B2 | * | 10/2012 | Cloutier et al. | 374/161 |
| 8,558,203 B1 | * | 10/2013 | Gardner | G01J 3/10 250/365 |
| 2001/0056278 A1 | * | 12/2001 | Nield | A61B 18/22 606/15 |
| 2002/0123696 A1 | * | 9/2002 | Kokate | A61B 5/01 600/549 |
| 2003/0158591 A1 | * | 8/2003 | Brett | A61B 18/04 607/89 |
| 2003/0216720 A1 | * | 11/2003 | Sinofsky | 606/11 |
| 2005/0137587 A1 | * | 6/2005 | Nield | A61B 18/22 606/15 |
| 2005/0222559 A1 | * | 10/2005 | Shiono | A61B 18/24 606/16 |
| 2008/0192778 A1 | * | 8/2008 | Ohsono et al. | 372/6 |
| 2009/0022205 A1 | * | 1/2009 | Comendant | G01K 1/143 374/161 |
| 2009/0027873 A1 | * | 1/2009 | Tarlton | G02B 6/0003 362/84 |
| 2009/0135880 A1 | * | 5/2009 | Ichida | G01K 11/3213 374/161 |
| 2009/0177191 A1 | * | 7/2009 | Brown | 606/12 |
| 2009/0302237 A1 | * | 12/2009 | Bortz | C09K 11/02 250/473.1 |
| 2010/0274235 A1 | * | 10/2010 | Mihajlovic | A61B 5/0084 606/15 |
| 2011/0213349 A1 | * | 9/2011 | Brown | A61B 18/22 606/10 |
| 2012/0134621 A1 | * | 5/2012 | Haslinger | G01B 1/00 385/12 |

OTHER PUBLICATIONS

Phosphor thermometry.*

R.W. Hermann et al; "Insertion Sheaths Prevent Breakage of Flexible Ureteroscopes Due to Laser Fiber Passage: A Video-Endoluminal Study of the Working Channel,"; J. Endourol 1747-51 (2010).

* cited by examiner

Step 1. Form fiber with ball-tip

Step 2. Flatten end to create chamfer

FIG. 4

PROTECTIVE SHEATH AND METHOD OF USING SAME FOR LASER SURGERY

This application claims the benefit of provisional U.S. Patent Application Ser. Nos. 61/721,184, filed Nov. 1, 2012; 61/674,058, filed Jul. 20, 2012; and 61/596,000, filed Feb. 7, 2012, each of which is incorporated herein by reference.

BACKGROUND OF THE INVENTION

1. Field of the Invention

This invention relates to devices and methods for delivering therapeutic light to a tissue, and in particular to optical fiber arrangements in which a protective sheath is placed over the fiber prior to insertion into an endoscope that guides the fiber to a treatment site. The protective sheath prevents mechanical damage to working channel of the endoscope during insertion of the fiber, insulates the fiber from surrounding cooling fluids, protects the fiber when it is extended outside the scope, and may serve as an indicator of overheating that enables early detection of excess heating or burning of tissues or equipment at the treatment site. Preferably, the protective sheath is designed to be as thin as possible so that it does not impede flow of irrigation fluid to the treatment site or limit the flexibility of the fiber.

The material of the sheath is preferably selected to have a thermal signature that enables radiation emitted by the sheath as a result of overheating to be distinguished from radiation normally emitted during treatment. The thermal signature may, for example, be distinguishable by frequency domain analysis, rather than just by timing or amplitude, so as to ensure that detection of overheating is not affected by changes in radiation emitted during treatment due to changes in the tissue being treated, contact between the laser and the tissue (as frequently occurs during treatment of stones), or variations in the laser radiation applied to the treated tissue. In addition, the present invention may be used in connection with the inventor's Smart Fiber technology, in which a phosphor material is added to the fiber's buffer or cladding to provide light emission at a predetermined frequency/wavelength when too much errant laser energy is present and/or when overheating occurs, the sheath itself may include one or more phosphor materials that emit visible or infrared light at a particular frequency or wavelength in response to stimulation by temperature or radiation to provide an easily-observed indication of conditions at the treatment site, based on the color or frequency/wavelength of the light transmitted back to a surgeon or detection device at the input end of the scope, and/or such phosphor materials may be included in the catheter or introducer.

Additional features of the invention may include some or all of the following features: (a) trim markings at a distal end of a protective sheath, and/or provision of a cutting guide device, so that the protective sheath can easily be adapted for use with ureteroscopes and other endoscopes of different lengths; (b) arrangement of the sheath to glow if a fiber is pulled too far into the sheath, thereby providing a visual warning and protection for the scope is the fiber is pulled in too far, even when the field of view is otherwise cloudy due to the effects of the surgical procedure; (c) an arrangement and method of utilizing the protective sheath, in which liquid is drawn into the sheath by providing a tight fit between the outer diameter of the fiber and the inner diameter of the sheath that causes irrigation fluid to be drawn into the sheath as the fiber is pulled into the sheath; (d) modification of the fiber to include a ball or spherical tip with a flattened end; and (e) inclusion of perforations, apertures, or holes along the length of the sheath to improve sterilization efficiency.

2. Description of Related Art

It is known that protective sheaths may be used to protect the working channel of endoscopes and similar devices from damage caused during insertion of the fiber into the channel, and to provide an early warning that overheating is occurring by emitting radiation that has a different thermal signature than the radiation resulting from normal treatment. See, e.g., copending U.S. patent application Ser. No. 13/127,911, filed May 5, 2011 (based on PCT Appl. No. PCT/US2009/006021) and the article by R. W. Herrmann et al. entitled *"Insertion Sheaths Prevent Breakage of Flexible Ureteroscopes Due to Laser Fiber Passage: A Video-Endouminal Study of the Working Channel,"* Journal of Endourology, Vol. 24, No. 11, November 2010. In addition, see copending PCT Appl. No. PCT/US2009/006021, filed Nov. 6, 2009.

While such a sheath may provide good protection against mechanical damage to the scope or other instrument through which the fiber is inserted, however, the prior protective sheath designs have a number of disadvantages that have limited their applicability.

The first problem addressed by the present invention is that the previously proposed protective sheaths have the disadvantage that they impede flow of irrigation fluid past the sheath. While it has been proposed in the above-mentioned copending PCT Appl. No. PCT/US2009/006021 to reduce the wall thickness of the sheath, such reduction in the wall thickness of the sheath makes it difficult to detect emission of radiation from the sheath by conventional amplitude detection, especially in applications where the intensity of treatment radiation observed through the scope varies greatly due to changes in the tissue being treated and especially during contact between the fiber and the tissue. The Applicant has discovered that in may laser surgery procedures, such as urological stone removal, it is common for the fiber to actually contact the tissue, making it extremely difficult using conventional monitoring methods to distinguish emissions from the sheath itself that indicate overheating and potential damage to tissues or instruments.

The second problem addressed by the present invention is that endoscopic instruments, such as flexible ureteroscopes, have different lengths for different applications and patients. The need to manufacture, purchase, and stock scopes of different lengths has resulted in increased costs to both manufacturers and users. The present invention addresses this problem by permitting manufacture of the sheaths in one or just a few standard lengths, and providing trim markings to indicate proper lengths to enable the user to more easily trim the sheaths to the desired length using a cutting instrument such as a knife or scissors. Alternatively, the problem is addressed by providing a cutting guide that facilitates trimming of the sheaths to the appropriate lengths.

The third problem addressed by the present invention is that it is often difficult, due to debris obscuring the field of vision or excessive light from the glowing tissues or the laser itself, for a surgeon to determine the exact position of a laser-delivery fiber end relative to the scope. As a result, it is common for surgeons to pull the fiber tip slightly into the scope in order to the field of view, which can decrease the useful life of the fiber and present a danger of overheating. The present invention addresses this problem in two ways. The first is to improve visibility by arranging the sheath to glow during a treatment procedure, improving the visibility of the fiber tip so that it is not necessary to pull the tip into the scope for reference during treatment, and the second is to provide a tight fit between the sheath and the scope to cause a suction effect that draws cooling fluid into the sheath to help prevent overheating when the fiber is pulled a small distance into the sheath, whether intentionally or unintentionally.

The fourth problem addressed by the present invention relates to the use of spherical or ball shape fiber tips to enhance the protective effects of the fiber-length by facilitating insertion of the fiber/sheath combination into the endoscope, and by providing further protection from erosion of the fiber due to entry of reflected energy into the cladding and resultant overheating. The problem is that, in practice, it has been found that the spherical or ball-shaped fiber tip can itself be a source of overheating, caused by internal reflections within the fiber tip. The present application addresses this problem by modifying the spherical or ball-shaped fiber tip to include a flattened end. Preferably, the spherical or ball-shaped tip is formed first, and then the end of the sphere or ball shape is flattened to provide a hybrid spherical/chamfered structure.

SUMMARY OF THE INVENTION

It is accordingly an objective of the invention to provide a protective sheath for a fiber that protects a surgical device, such as an endoscope, through which the fiber is inserted from mechanical damage, and yet that does not impede flow of irrigating fluid past the fiber or limit the flexibility of the fiber.

It is a second objective of the invention to provide a protective sheath for a fiber that, when overheated, emits radiation that can readily be distinguished from radiation emitted as a result of normal treatment, the presence of radiation from the sheath providing an early warning that overheating is beginning to occur at the treatment site.

It is a third objective of the invention to provide a protective sheath for a fiber, and/or a protective sheath cutting guide, that facilitates cutting of the sheath to different lengths for use with different scopes, so that a sheaths having standard lengths can be customized by a user to fit the different scopes.

It is a fourth objective of the invention to provide a protective sheath for a fiber that glows whenever the fiber is pulled into the sheath in order to provide an indication that the fiber has been drawn into the sheath even when the end of the fiber is obscured by a cloudy environment.

It is a fifth objective of the invention to provide an arrangement or treatment method that provides added protection from damage due to overheating by drawing irrigation fluid into the sheath whenever the fiber tip is pulled into the sheath. This arrangement and method can be used not only to prevent damage to the fiber or sheath, but also to provide a means of controlling a temperature of the fiber during lasing so that the treatment period can be extended.

The first two objectives of the invention are achieved by a protective sheath arrangement in which a sacrificial sheath is placed over the entire length of the fiber to prevent mechanical damage to the working channel of the instrument through which the fiber is inserted, and to insulate the fiber from the surrounding fluids, the sheath being supported by the fiber itself to enable the sheath to made of a relatively thin material that does not impede flow of fluid past the sheath, and the sheath preferably having a thermal signature that can readily be distinguished from that of tissues subject to treatment, even when the fiber is in contact with the tissue. In order to be distinguishable in such a situation, the radiation emitted by the sheath preferably has a characteristic signature that is different from the treatment radiation, and independent of amplitude. This signature can be detected by analyzing the frequency spectrum or shape of the emitted radiation waveform, for example by Fourier analysis, or by selecting sheath materials that emit light at a particular characteristic frequency or frequencies. Such materials may be formed by adding dopants or coatings to the base polyamide, polyimide, or PET material of the protective sheath. The dopants may include phosphorescent materials that glow at a characteristic frequency when heated to a predetermined temperature or irradiated with the treatment laser wavelength, e.g., 2.1 microns, so that the detection of a particular color in the radiation visible through the scope provides an indication of temperature. By adding multiple phosphors, the monitor can detect a temperature progression and responses to actions such as pull back or reduction in treatment laser intensity, or changes in the tissues being treated.

The second, third, and fourth objectives of the invention are also achieved, in accordance with the principles of additional preferred embodiments of the invention, by protective sheath arrangements in which: (a) a protective sheath is provided with markings that serve as guides for cutting the sheath to lengths corresponding to those of different scopes in which the protective sheath may be used; (b) a protective sheath is arranged to glow when a fiber is withdrawn into the sheath during lasing, so as to increase the visibility of the fiber tip; and the protective sheath is tightly fitted into the scope such that, as the sheath is withdrawn into the scope, a plunger effect results to draw irrigation fluid into the scope. It will be appreciated by those skilled in the art that these three embodiments may be used in combination or separately, and with the specific protective sheaths described in this application or with other protective sheaths.

Still further advantages are achieved by an embodiment in which an optical fiber with a generally spherical or ball-shaped tip is provided, the optical fiber having a flattened end. According to a preferred method of making the optical fiber of this embodiment, the spherical or ball-shaped tip (or hemispherical or rounded tip) is formed first. The flattened end is then formed in the spherical or ball-shaped (or otherwise rounded) tip by a suitable method such as polishing or cutting. The fiber tip of this embodiment may be used in connection with the inventor's Smart Fiber technology, in which a phosphor material is added to the fiber's buffer or cladding to provide light emission at a predetermined frequency/wavelength when too much errant laser energy is present and/or when overheating occurs, and is not necessarily limited to the specific fibers or fiber/sheath arrangements disclosed in the present application, but rather are applicable to any optical fiber having a spherical, ball-shaped, or otherwise rounded tip through which energy is delivered for surgical or therapeutic purposes, and that may be subject to undesired overheating.

Finally, the invention also provides for the optional inclusion of perforations in the protective sheath, so as to improve sterilization efficiency, as well as other advantageous features described in connection with specific preferred embodiments of the invention and the accompanying drawings.

DETAILED DESCRIPTION OF THE PREFERRED EMBODIMENTS

Figure 1A:
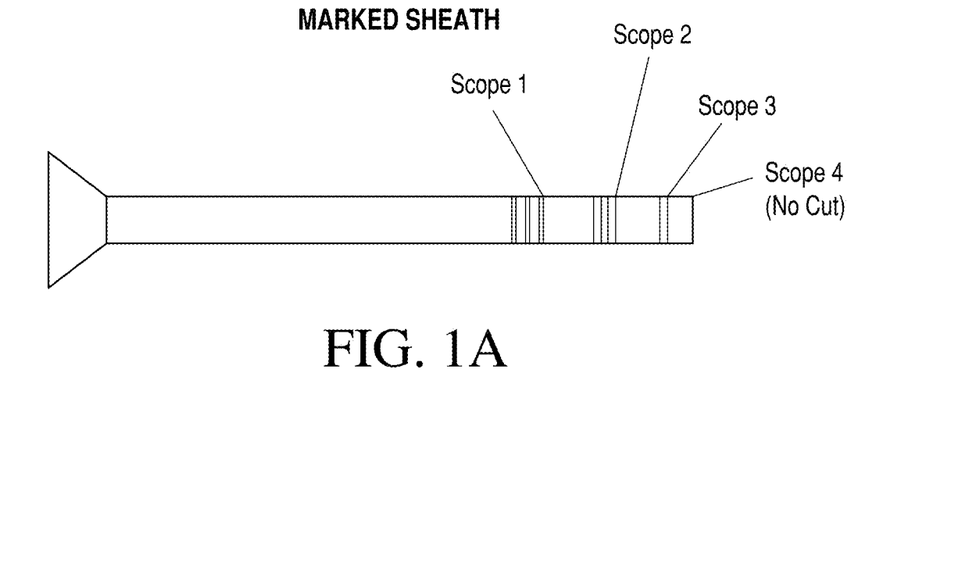
FIG. 1A is a plan view of sheath with trim markings according to a preferred embodiment of the present invention.

FIG. 1A shows a fiber sheath with trim markings labeled Scope 1, Scope 2, Scope 3, and Scope 4. The sheath illustrated in FIG. 1A may include the characteristics of extending the length of the fiber and/or of including phosphors according to preferred embodiments of the invention, as described below, although it will be appreciated by those skilled in the art that the trim markings illustrated in FIG. 1A are themselves optional and may be used both with protective sheaths having the characteristics of extending the length of the fiber and/or including phosphors, or with sheaths that do not include those characteristics.

By extending the lengths of the protective sheath shown in FIG. 1A over the entire length of the fiber, it is possible to prevent mechanical damage caused when the sharp edges of the fiber tip perforates the scopes soft plastic working channel. This is particularly the case when the scope is fully deflected and the fiber tip scores the inside of a plastic working channel, which can cause contaminants to accumulate. To prevent the fiber's sharp edges from contacting the endoscope working channel surface, the parent application, the protective sheath is placed over the entire length, or substantially the entire length, of the fiber. Such a sheath may be made of, but is not limited to, a base material such as polyamide, polyimide, and polyethylene teraphthalate (PET), with appropriate dopants as discussed below.

Figure 1B:
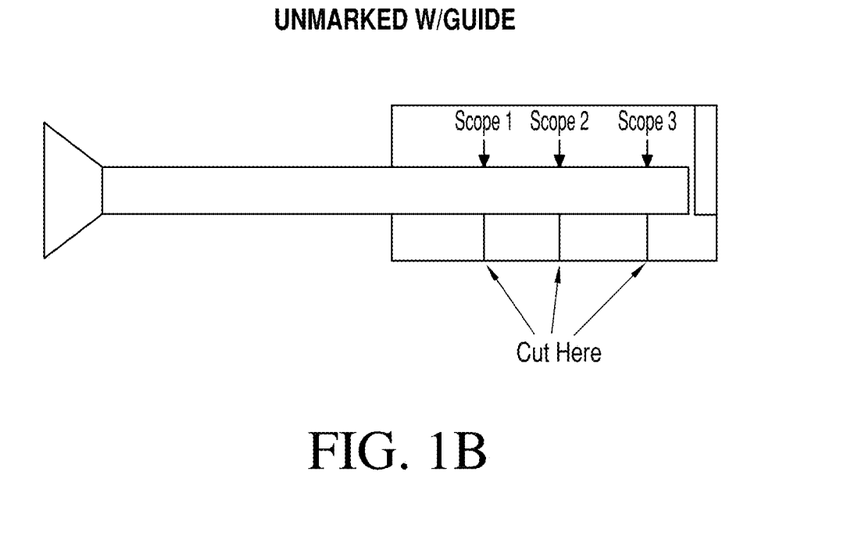
FIG. 1B is a plan view of an unmarked sheath and cutting guide in accordance with the principles of a second preferred embodiment of the present invention.

To ensure optimal flexibility and size, the protective sheath is sized for individual fibers, so that the fiber and sheath are very close in size and the fiber, with the fiber being inserted into the sheath before insertion of the sheath into the working channel of an endoscope or introducer. This sizing may be achieved, as described in more detail below, by inclusion of trim markings on the sheath, as shown in FIG. 1A, or by an appropriate trimming device, as shown in FIG. 1B.

To ensure that the protection sheath will not interfere with flow of liquid, the protective sheath may be made thin enough to collapse when not fitted over a fiber. By way of example, for ureteroscopic or laser lithotripsy applications, the protective sheath may have wall thickness of less than 100 µm, and preferably less than 25 µm.

By providing a protective sheath that is longer than the scope in which it is to be inserted, the protective sheath not only limits mechanical damage to the working channel of the scope during insertion of the fiber, but also damage that can result if the fiber is prematurely pulled back into the scope while a procedure is being performed. Moreover, the extended sheath may improve visualization of the treatment site by the surgeon by providing a light shielding effect to reduce the amount of light that reaches the treatment side imaging camera. Still further, the relatively thin sheath of the invention may actually improve steerability of the fiber because of the increased outer diameter of the fiber/sheath combination relative to the original fiber diameter.

In addition to protecting the working channel of the scope or introducer through which the fiber is introduced to the treatment site, a protective sheath such as the one illustrated in FIG. 1A, or other protective sheaths, may be arranged to provide an early warning of overheating by including in the sheath, or making the sheath out of, a material that emits radiation having a characteristic signature as the temperature of the sheath rises. However, unlike the sheath and monitoring method disclosed in copending U.S. patent application Ser. No. 13/127,911, filed May 5, 2011, and incorporated herein by reference, the protective sheath of the present invention may have a signature that can be detected in a treatment environment where amplitude or timing of emitted radiation signals cannot be used to distinguish overheating of the sheath from fluctuations in the treatment radiation, or fluctuations in radiation emitted by treated tissues, that occur during a normal treatment procedure. Such fluctuations typical occur, by way of example and not limitation, during urological stone-removal procedures, during which it is typical for the optical fiber to contact the stone being vaporized, causing wide variations in radiation detected during monitoring.

In order to be distinguishable in such a situation, the radiation emitted by the protective sheath must have a characteristic signature that is different from the treatment radiation, and independent of amplitude. This signature can be detected by analyzing the frequency spectrum or shape of the emitted radiation waveform, for example by Fourier analysis, or by selecting sheath materials that emit light at a particular characteristic frequency or frequencies.

Methods of achieving a characteristic signature include adding dopants or coatings to the material of the protective sheath. The dopants may include phosphorescent materials that glow at a characteristic frequency when heated to a predetermined temperature or exposed to a primary laser wavelength, so that the detection through the scope of a particular color or wavelength/frequency in the visible or IR radiation provides an indication of temperature. By adding multiple phosphors, the monitor can detect a temperature progression and responses to actions such as pull back or reduction in treatment laser intensity, or changes in the tissues being treated.

The monitoring/analysis method used with a protective sheath having the above described emission characteristics will depend on the emission signature of the sheath, and on the nature of the treatment. If phosphors are used, monitoring may be carried out in low power applications entirely by having the operator watch for visible color changes. On the other hand, very subtle characteristic signatures, or changes in the presence of a high intensity or highly variable background, may be detected by signal processing methods such as Fourier frequency spectrum analysis.

Those skilled in the art will appreciate that the protective sheath described herein may be used in connection with other monitoring methods or structures, including coatings on instruments or the addition of phosphors to the fiber itself, in order to provide more detailed monitoring of conditions at the treatment site and problems with the surgical instrumentation.

The trim markings Scope 1, Scope 2, Scope 3, and Scope 4 illustrated in FIG. 1A indicate where to cut the sheath to achieve sheath lengths appropriate to a particular scope.

Such trim markings may be printed or may include grooves, ridges, or other structures embossed into or otherwise formed in the sheath. As a result of the illustrated arrangement, the sheath can be cut to an appropriate length by the user with a blade, scissors, or other cutting device, eliminating the need for the user to purchase and stock sheaths of different lengths, thereby reducing costs.

The number and configuration of the different trim markings is illustrative only, and may be varied depending on the number and configurations of the different scopes with which the sheath is to be used. It will be appreciated that the trim markings of the present invention may be used on the sheath described in parent provisional U.S. patent application Ser. No. 61/596,000 or on other protective sheaths whose lengths is determined by the scope in which they are to be inserted.

As an alternative to markings on the protective sheath itself, as illustrated in FIG. 1A, the sheath may be left unmarked and a trim guide may be provided, as illustrated in FIG. 1B. The trim guide can take any form so long as it includes a marking or structure against which the end of the sheath is placed, and markings to indicate where the fiber should be cut for different scopes (scope1, scope2, scope3). Again, the markings may be printed or in the form of structures such as grooves, and the number of markings may be varied depending on the number of scopes with which the protective sheath can be used.

The protective sheath of FIG. 1A can be arranged, as illustrated in FIG. 1B, to further prevent damage from unintentional or intentional withdrawal of the fiber into the sheath or scope during lasing, by arranging the protective sheath to glow with increased intensity when the fiber is withdrawn into the sheath, so that the tip of the fiber may be more easily distinguished, even in an obscured environment.

Figure 2A:
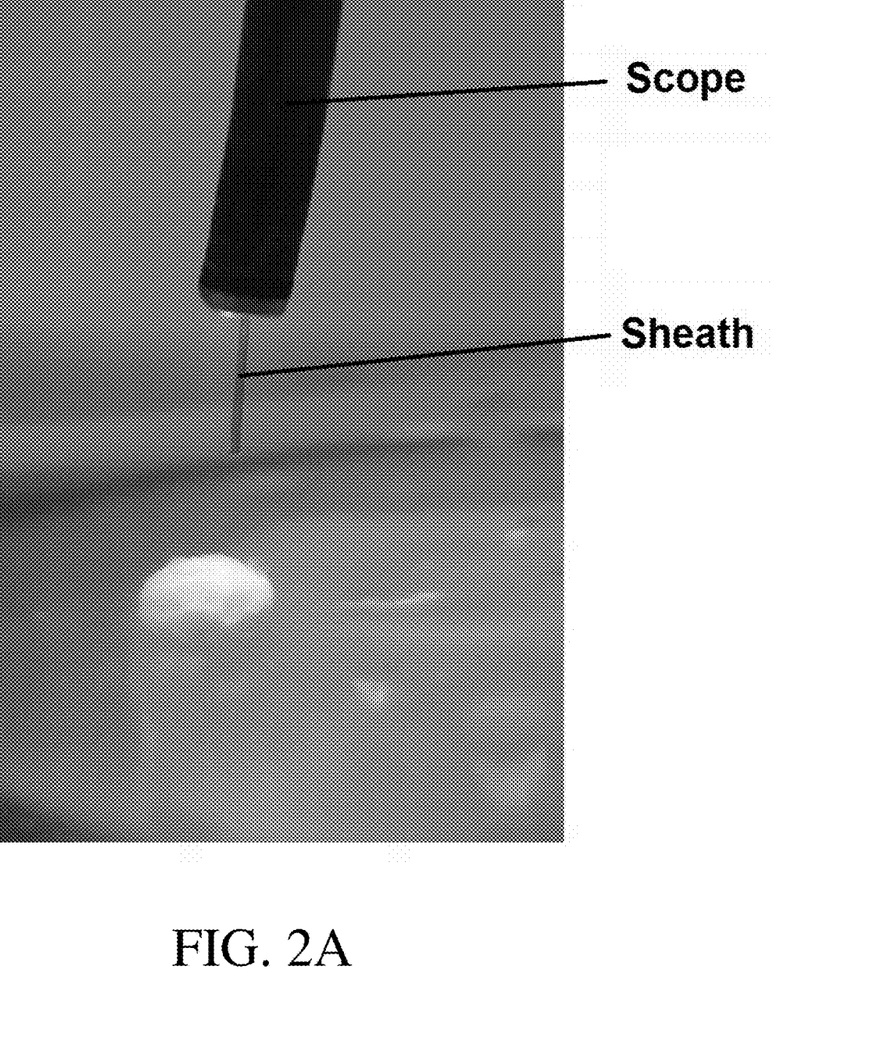
FIG. 2A is a photo of a sheath that surrounds a fiber and that has been extended outside the scope, before lasing.
Figure 2B:
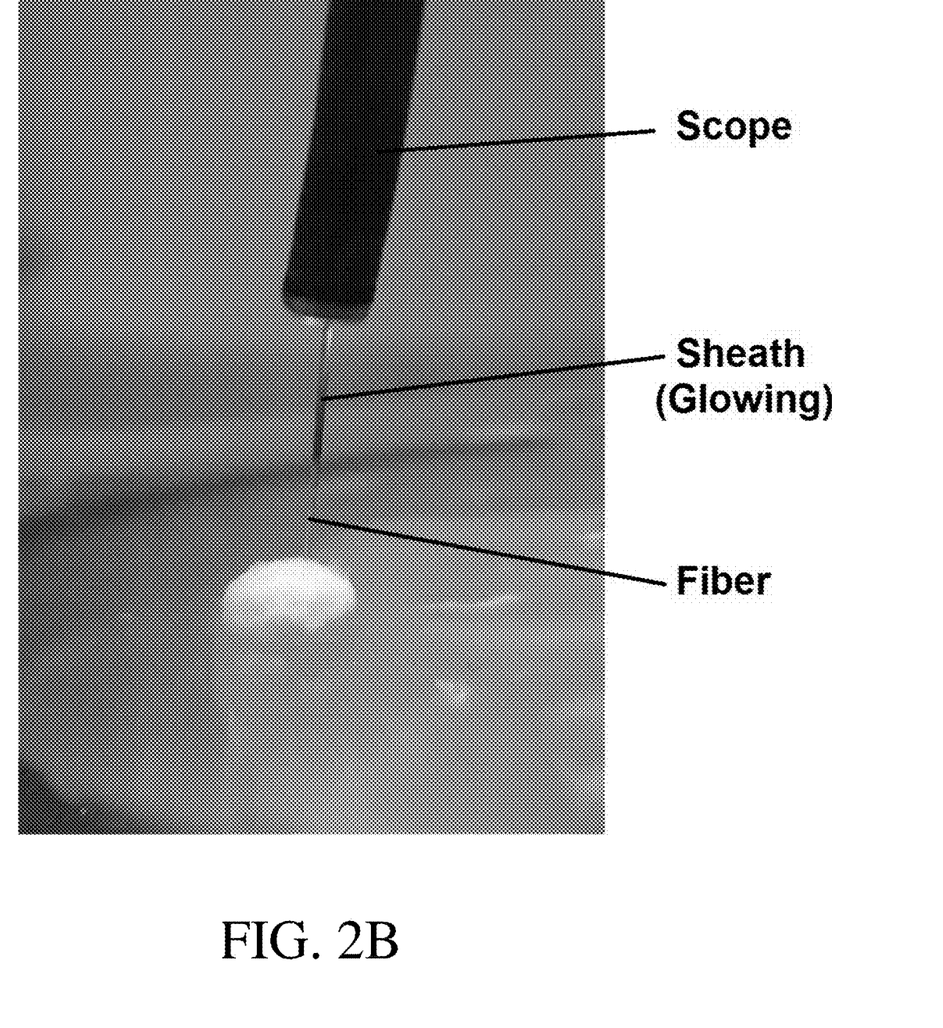
FIG. 2B is a photo of the sheath, showing a fiber that has been extended outside the sheath during lasing.
Figure 3A:
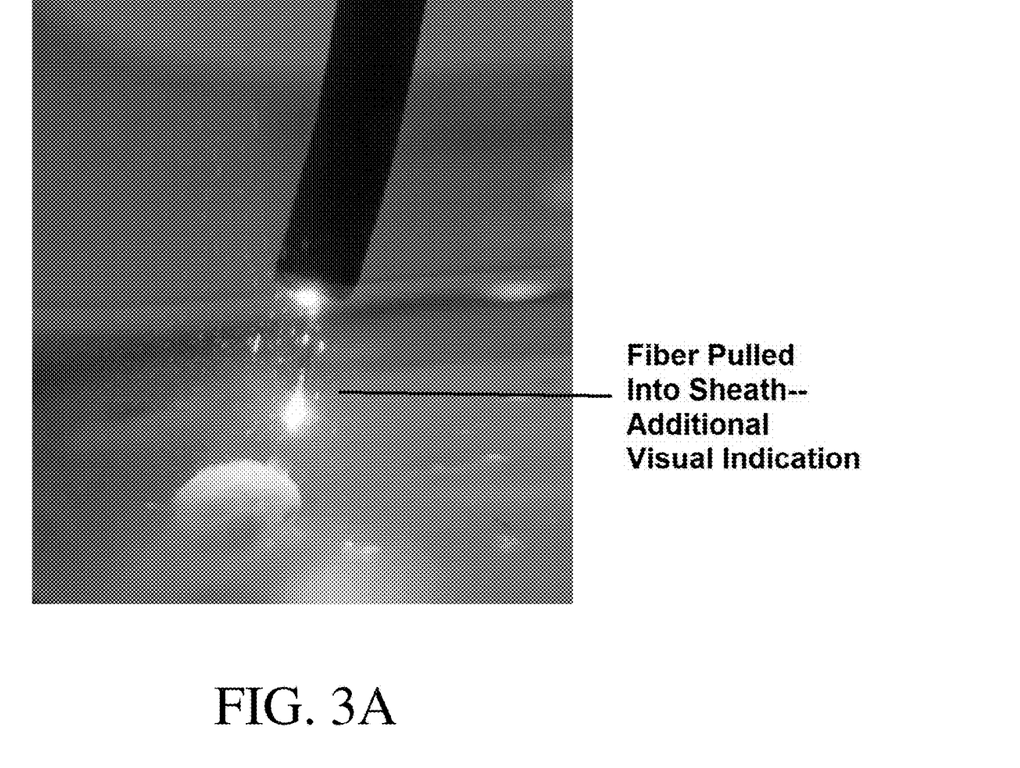
FIG. 3A is a photo of a sheath and fiber, in which the fiber has been withdrawn into the sheath during lasing and the sheath has begun to glow.
Figure 3B:
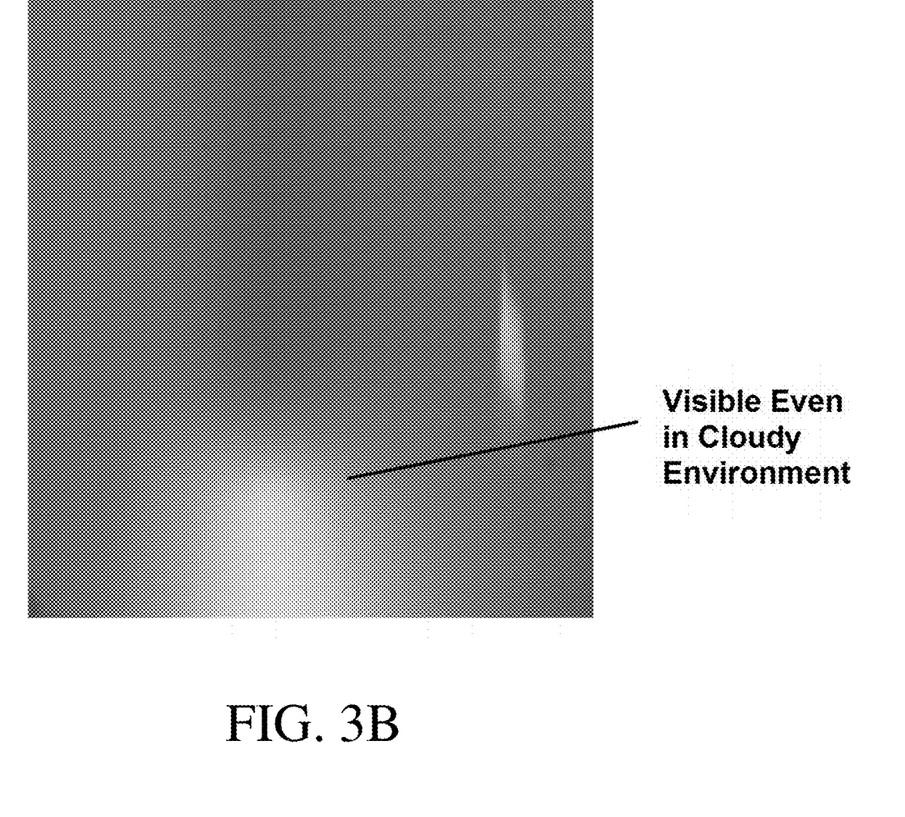
FIG. 3B shows the sheath and fiber in a view identical to that of FIG. 3C, but in a cloudy or obscured environment.

As shown in FIGS. 2A, 2B, 3A, and 3B, the protective sheath of FIG. 1A can be arranged to emit light during a lasing procedure by, for example, coating the fiber with a phosphor that glows in response to radiation emitted by the fiber during lasing. In order to provide a further visual indication of the tip of the fiber, the sheath may be arranged to emit a brighter glow as shown in FIG. 2B, for example by means of a material such as a phosphor coated onto or included in the material of the sheath and that emits radiation in response to the increased heat that occurs when the fiber is withdrawn into the sheath, as illustrated in FIG. 3A. As illustrated in FIG. 3B, the glow can be made bright enough to be visible even when the tip of the fiber would otherwise be obscured by debris or vaporized tissue at the treatment site.

According to another preferred embodiment of the invention, the protective sheath illustrated in FIG. 1A, or other protective sheaths without trim markets, may be arranged such that the outer diameter of the fiber is closely fitted to the inner diameter of the sheath, so that when the fiber is drawn into the sheath, a suction or plunger effect is created that draws irrigation fluid into the sheath to provide a cooling effect. This allows the temperature of the fiber and sheath to be more precisely controlled and enabling the treatment time to be extended if desired, by reducing overheating of the fiber and sheath.

Figure 4:
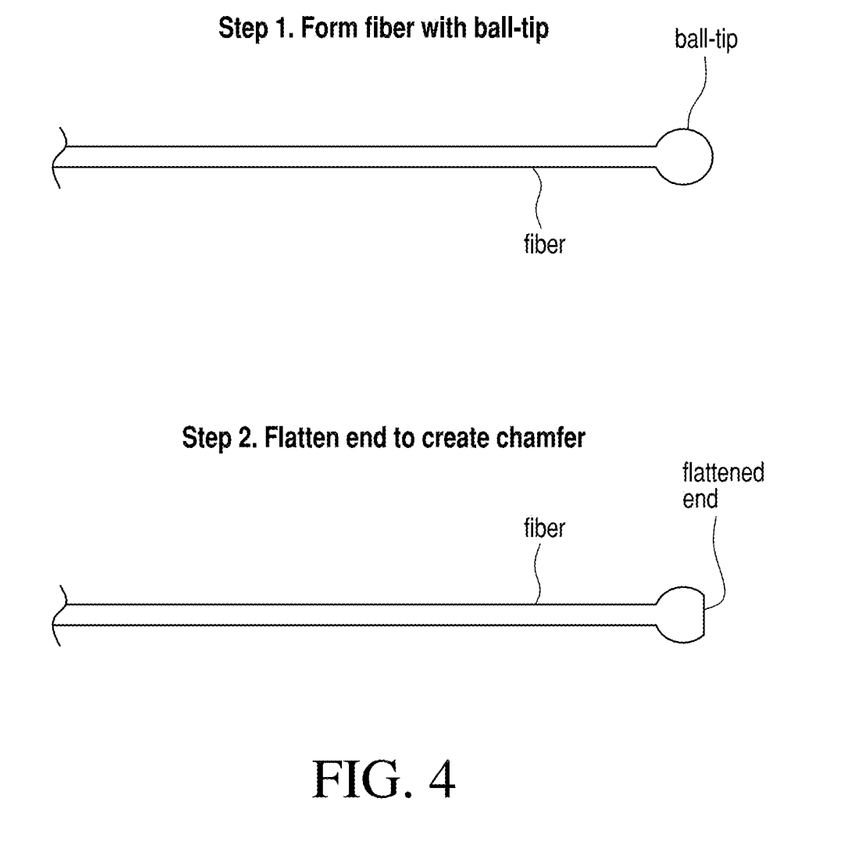
FIG. 4 illustrates the process of flattening a spherical tip of an optical fiber in accordance with a preferred embodiment of the present invention.

According to the principles of yet another the preferred embodiment of the invention, illustrated in FIG. 4, the silica tip of an optical fiber to be used with a protective sheath of the type described, or to be used without such a sheath, may be formed into an at least partially spherical or ball shape, as indicated by step 1 of FIG. 4. The spherical or ball-shape is then further processed by flattening the end of the fiber to form a planar surface and a chamfer, as indicated by step 2 of FIG. 4. In this embodiment, the sides of the fiber tip remain rounded to facilitate insertion into an endoscope and deflect radiation incident on the outside of the tip from being deflected into, and therefore potentially eroding, the cladding. However, the flattened of the fiber allows the deflected radiation to exit the fiber tip rather than being internally reflected, thereby preventing overheating due to the internal reflections.

According to yet another advantageous modification of the protective sheaths described above, or other similar protective sheaths, the protective sheaths may be provided with perforations to improve sterilization efficiency.

Although specific embodiments of the invention have been described in connection with the accompanying drawings, it will be appreciated that the invention is not to be limited the specific embodiments disclosed herein.

I claim:

1. An optical fiber arrangement for use in laser surgery applications, said arrangement including:
   an optical fiber for supplying therapeutic radiation to a treatment site during a surgical procedure; and
   a protective sheath into which is configured to be placed over the optical fiber prior to insertion of the protective sheath and the optical fiber into a scope or introducer in order to protect a working channel of the scope or introducer during insertion of the protective sheath and optical fiber, wherein
   wherein the optical fiber is configured to be extended from and retracted into a distal end of the protective sheath during a surgical procedure following insertion of the protective sheath and optical fiber through the scope or introducer to a treatment site, and
   wherein the protective sheath is made of a material having the property of a thermal emission signature that enables radiation emitted by the material of the sheath to be distinguished from other radiation at the treatment site by a waveform shape or frequency spectrum of the radiation emitted by the material of the sheath, independent of an amplitude of the radiation emitted by the material of the sheath.

2. The arrangement of claim 1, wherein the sheath has a wall thickness of less than 100 μm.

3. The arrangement of claim 2, wherein the sheath has a wall thickness of less than 25 μm.

4. The arrangement of claim 1, wherein said laser surgery applications include ureteroscopy and laser lithotripsy.

5. The arrangement of claim 1, wherein said thermal emission signature is a visible or infrared light emission signature resulting from the addition of at least one phosphorescent material to the sheath.

* * * * *